United States Patent
Costantini et al.

[11] Patent Number: 6,147,256
[45] Date of Patent: Nov. 14, 2000

[54] CO/CR CATALYZYED OXIDATION OF CYCLOHEXANE

[75] Inventors: Michel Costantini, Lyons; Eric Fache, Caluire et Cuire, both of France

[73] Assignee: Rhodia Fiber and Resin Intermediates, France

[21] Appl. No.: 09/058,175

[22] Filed: Apr. 10, 1998

[30] Foreign Application Priority Data

Apr. 10, 1997 [FR] France .................................. 97 04637

[51] Int. Cl.⁷ .......................... C07C 51/31; C07C 51/215
[52] U.S. Cl. ............................................ 562/543; 562/542
[58] Field of Search ..................................... 562/542, 543

[56] References Cited

U.S. PATENT DOCUMENTS 3,987,100  10/1976  Barnette et al. .
4,902,827   2/1990  Steinmetz et al. ...................... 562/543

FOREIGN PATENT DOCUMENTS 0021118   7/1981  European Pat. Off. .
929213    5/1982  U.S.S.R. .
0415172   8/1934  United Kingdom .
0086951  10/1967  United Kingdom .

*Primary Examiner*—Gary Geist
*Assistant Examiner*—Rosalynd Keys
*Attorney, Agent, or Firm*—Norman H. Stepno, Esq.

[57] ABSTRACT

Carboxylic acids, e.g., adipic acid, are more selectively prepared by oxidizing cyclohexane with oxygen or an oxygen-containing gas, in liquid phase, in a solvent reaction medium which comprises a polar protic or aprotic solvent, and also in the presence of a catalytically effective amount of catalyst values dissolved in said solvent reaction medium, the catalyst values comprising at least one solvent-soluble cobalt compound and at least one solvent-soluble chromium compound.

18 Claims, No Drawings

CO/CR CATALYZYED OXIDATION OF CYCLOHEXANE

CROSS-REFERENCE TO PRIORITY APPLICATION

This application claims priority under 35 U.S.C. §119 of FR-97/04637, filed Apr. 10, 1997, hereby expressly incorporated by reference and relied upon.

BACKGROUND OF THE INVENTION

1. Technical Field of the Invention

The present invention relates to the oxidation, with oxygen or an oxygen-containing gas, of hydrocarbons and/or alcohols and/or ketones into the corresponding carboxylic acids.

2. Description of the Prior Art

The direct $O_2$ oxidation of hydrocarbons, more particularly cycloalkanes, in the presence of a catalyst, is a process which has long been known to this art. The reason for this is that there are many obvious advantages in avoiding the use of an oxidizing agent such as nitric acid, currently in industrial favor, thereby avoiding the treatment of the nitrogen oxides generated.

In the many variants of such a process of catalytic oxidation by means of oxygen, cobalt is the catalyst most frequently of choice.

Thus, U.S. Pat. No. 2,223,493 describes the oxidation of cyclic hydrocarbons into the corresponding diacids, in a liquid phase generally containing acetic acid, at a temperature of at least 60° C., using a gas containing oxygen and in the presence of an oxidation catalyst such as a cobalt compound.

U.S. Pat. No. 3,987,100 describes a process for preparing cyclohexanone and cyclohexanol by reacting cyclohexane with oxygen, in at least three successive steps, at a temperature of 130° C. to 180° C. and under a pressure of about 4 to 25 bar and in the presence of very small amounts of a catalytic system comprising cobalt and chromium. This process is carried out in the absence solvent and does not permit adipic acid to be prepared directly.

GB-A-1,086,951 describes the combined oxidation of mixtures of cyclohexanol and an aldehyde, in the liquid phase, with oxygen, in the absence or presence of a catalyst comprising at least one transition metal compound. This process produces cyclohexanone, epsilon-caprolactone and dicarboxylic acids starting from cyclohexanol, as well as the monocarboxylic acid corresponding to the aldehyde employed.

U.S. Pat. No. 4,902,827 describes an improvement in the air-oxidation of cyclohexane into adipic acid, in a liquid phase containing acetic acid, at a temperature of 80° C. to 160° C. and in the presence of an oxidation catalyst comprising a soluble cobalt compound and a soluble zirconium and/or hafnium compound.

And, more recently, EP-A-0,694,333 describes a catalyst comprising a cobalt salt and a ferric salt for the oxidation of hydrocarbons with oxygen.

Nonetheless, the selectivities attained employing the aforesaid prior art catalytic systems remain inadequate.

SUMMARY OF THE INVENTION

Accordingly, a major object of the present invention is the provision of a selectivity-improved process for the oxidation of hydrocarbons, alcohol and/or ketones into their corresponding carboxylic acids, by means of oxygen or an oxygen-containing gas, in the liquid phase, in a solvent medium selection from among the polar protic solvents and polar aprotic solvents and in the presence of a catalyst dissolved in the reaction medium, said catalyst comprising at least one soluble cobalt compound and at least one soluble chromium compound.

DETAILED DESCRIPTION OF BEST MODE AND SPECIFIC/PREFERRED EMBODIMENTS OF THE INVENTION

More particularly according to the present invention, the hydrocarbon starting substrates are advantageously alkanes, cycloalkanes, alkylaromatic hydrocarbons, alkenes and cycloalkenes, having from 3 to 20 carbon atoms.

Among these hydrocarbons, the cycloalkanes, in particular those having from 5 to 12 carbon atoms, are certainly the most commercially important, since their oxidation provides dicarboxylic acids and, in lesser proportions, intermediate cycloalkanols and cycloalkanones.

The most advantageous hydrocarbon is cyclohexane, the oxidation of which provides adipic acid, one of the base compounds for the synthesis of polyamide or nylon 6—6.

The subject process is also useful for the oxidation of the intermediate alcohols or ketones, in particular cycloalkanols and cyclohexanones having from 5 to 12 carbon atoms, in order to prepare the corresponding dicarboxylic acids. As will hereinafter be seen, the subject process will be described more particularly for the oxidation of hydrocarbons, essentially cycloalkanes, and more especially for the oxidation of cyclohexane.

The catalyst comprising at least one cobalt compound and a chromium compound makes it possible to directly prepare adipic acid with good selectivity, when the oxidation of cyclohexane is carried out; this capacity is obviously very advantageous from an industrial standpoint.

The catalyst comprises at least one cobalt compound which is soluble in the medium of reaction, selected, for example, from among cobalt chloride, cobalt bromide, cobalt nitrate, cobalt carboxylates such as cobalt acetate tetrahydrate, cobalt propionate, cobalt adipate, cobalt glutarate, cobalt succinate and cobalt chelates such as cobalt acetylacetonate.

The catalyst also comprises at least one chromium compound which too is soluble in the medium of reaction, selected, for example, from among chromium chloride, chromium bromide, chromium nitrate, chromium carboxylates such as chromium acetate, chromium propionate, chromium adipate, chromium glutarate, chromium succinate and chromium chelates such as chromium acetylacetonate.

The molar ratio between the chromium and the cobalt in the catalyst can vary over wide limits. It thus is possible to establish Cr/Co molar ratios ranging from 0.001 to 100 and preferably from 0.01 to 10.

The catalyst can be prepared in situ by introducing/charging the cobalt and chromium compounds into the reaction medium. It can also be prepared at the time of use by mixing said compounds in the proportions required to obtain the desired Cr/Co molar ratio. This admixing is more conveniently carried out in a solvent, preferably the solvent which will be used for the oxidation reaction.

The catalyst for the process of the invention can also comprise at least one zirconium and/or hafnium compound which is soluble in the reaction medium. Exemplary of such zirconium and hafnium compounds are zirconium tetrachloride, zirconium bromide, zirconium nitrate, zirconium carboxylates such as zirconium acetate, zirconium propionate, zirconium adipate, zirconium glutarate, zirconium succinate, zirconium chelates such as zirconium acetylacetonate, hafnium chloride, hafnium bromide, hafnium nitrate, hafnium carboxylates such as hafnium acetate, hafnium propionate, hafnium adipate, hafnium glutarate, hafnium succinate and hafnium chelates such as hafnium acetylacetonate.

The molar ratio between the zirconium and/or hafnium and the cobalt in the catalyst advantageously ranges from 0 to 10 and preferably from 0.001 to 5.

The amount of catalyst, expressed as a weight percentage of elemental cobalt and of elemental chromium relative to the total weight of the reaction mixture, ranges from 0.001% to 5% and preferably from 0.01% to 2%, these values, however, not being critical. What is important is only to have sufficient activity while at the same time not employing excessive amounts of a catalyst which then needs to be separated from the final reaction mixture and recycled.

It too is advantageous to employ an initiator compound for the oxidation reaction. Such initiators are typically hydroperoxides such as, for example, cyclohexyl hydroperoxide or tert-butyl hydroperoxide. These can also be ketones or aldehydes such as, for example, cyclohexanone, which is one of the compounds formed during the oxidation of cyclohexane, or acetaldehyde. Generally, the initiator constitutes from 0.01% to 20% by weight relative to the weight of the reaction mixture, these proportions also not being critical. The initiator is especially useful during the beginning of the oxidation and when the oxidation of cyclohexane is carried out at a temperature below 120° C. It can be introduced from the start of the reaction.

The liquid reaction medium contains an at least partial solvent for the carboxylic acid sought to be prepared via the process of the invention. This solvent can be very varied in nature, provided that it is not substantially oxidizable under the conditions of the subject reaction. It can be selected from among polar protic solvents and polar aprotic solvents. Exemplary polar protic solvents include carboxylic acids having only primary or secondary hydrogen atoms, in particular aliphatic carboxylic acids having from 2 to 9 carbon atoms, perfluoroalkylcarboxylic acids such as trifluoroacetic acid, alcohols such as tert-butanol, halogenated hydrocarbons such as dichloromethane, and ketones such as acetone. Exemplary polar aprotic solvents include lower alkyl esters (=alkyl radical having from 1 to 4 carbon atoms) of carboxylic acids, in particular aliphatic carboxylic acids having from 2 to 9 carbon atoms or perfluoroalkylcarboxylic acids, tetramethylenesulfone (or sulfolane), or acetonitrile.

Acetic acid is preferably employed as the solvent for the oxidation of cyclohexane. It is convenient to use a catalyst whose cobalt and chromium constituents are in the form of compounds derived from the carboxylic acid employed as the solvent, provided that said compounds are soluble in the reaction medium. For this reason, cobalt acetate and chromium acetate are thus preferred.

The solvent, as described above, advantageously constitutes from 1% to 99% by weight of the reaction medium, preferably from 10% to 90% and even more preferably from 20% to 80%.

The oxidation can also be carried out in the presence of water introduced from the initial stage of the subject process.

The temperature at which the oxidation reaction is carried out is variable, in particular depending on the substrate oxidized. It generally ranges from 50° C. to 200° C. and preferably from 80° C. to 140° C.

The pressure is also not a critical parameter of the subject process. It can be less than, equal to or greater than atmospheric pressure. Generally, it will range from 0.1 MPa (1 bar) to 20 MPa (200 bar), such values not being absolutely critical.

Pure oxygen, air, oxygen-enriched or oxygen-depleted air or, alternatively, oxygen diluted with an inert gas, can be used.

In order to further illustrate the present invention and the advantages thereof, the following specific examples are given, it being understood that same are intended only as illustrative and in nowise limitative.

EXAMPLE 1

The following reactants:
(i) 21.25 g (253 mmol) of cyclohexane,
(ii) 27.35 g of acetic acid,
(iii) 0.26 g (2.65 mmol) of cyclohexanone,
(iv) 0.32 g (1.29 mmol of Co) of cobalt acetate tetrahydrate, and
(v) 0.0331 g (0.1445 mmol of Cr) of chromium acetate, were introduced into a 125 ml titanium autoclave fitted with means for heating via a heating collar, a turbomixer and means for introducing gas and regulating the pressure.

After closing the reactor, it was stirred at 1,000 revolutions per minute, an air pressure (100 bar at 20° C.) was created and the reactor was heated. The temperature attained 105° C. in the bulk in 10 min and this temperature was maintained for an additional 50 min.

After cooling and depressurization, the reaction mixture comprised two liquid phases which were homogenized by addition of acetic acid.

The homogeneous mixture thus obtained was assayed by gas chromatography.

The following results were obtained:
(a) degree of conversion (DC) of the cyclohexane: 12.2%
(b) selectivity (CS) towards cyclohexanol relative to the cyclohexane converted: 6.2%
(c) selectivity (CS) towards cyclohexanone relative to the cyclohexane converted: 11.9%
(d) CS towards adipic acid relative to the cyclohexane converted: 67.3%
(e) CS towards adipic acid+cyclohexanone+cyclohexanol relative to the cyclohexane converted: 85.4%
(f) molar ratio of adipic acid/total of the diacids formed (adipic acid, glutaric acid and succinic acid): 85.3%
(G) CS towards other compounds (butyrolactone, valerolactone, hydroxyadipic acid, hydroxycaproic acid): 3.0%

Comparative Test 1

The procedure of Example 1 was repeated in the same apparatus and under the same operating conditions, but without charging any chromium compound and using an amount of cobalt acetate tetrahydrate increased by an amount equal to the molar amount of chromium acetate in Example 1.

The following results were obtained:
(a) degree of conversion (DC) of the cyclohexane: 15.0%
(b) CS towards cyclohexanol relative to the cyclohexane converted: 14.7%
(c) CS towards cyclohexanone relative to the cyclohexane converted: 8.1%
(d) CS towards adipic acid relative to the cyclohexane converted: 54.7%
(e) CS towards adipic acid+cyclohexanone+cyclohexanol relative to the cyclohexane converted: 77.5%
(f) molar ratio of adipic acid/total of the diacids formed: 82.6%
(g) CS towards other compounds: 10.9%

Comparative Test 2

Comparative Test 1 was repeated in the same apparatus and under the same operating conditions, but employing an even larger amount of cobalt acetate tetrahydrate (1.45 g).

The following results were obtained:
(a) degree of conversion (DC) of the cyclohexane: 13.2%
(b) CS towards cyclohexanol relative to the cyclohexane converted: 9.5%
(c) CS towards cyclohexanone relative to the cyclohexane converted: 8.5%
(d) CS towards adipic acid relative to the cyclohexane converted: 56.7%
(e) CS towards adipic acid+cyclohexanone+cyclohexanol relative to the cyclohexane converted: 74.7%
(d) molar ratio of adipic acid/total of the diacids formed: 81.2%
(e) CS towards other compounds: 12.2%

Comparative Test 3

The procedure of Example 1 was repeated in the same apparatus and under the same operating conditions, but replacing the chromium acetate by the same molar amount of iron acetate.

The following results were obtained:
(a) degree of conversion (DC) of the cyclohexane: 15.0%
(b) CS towards cyclohexanol relative to the cyclohexane converted: 9.3%
(c) CS towards cyclohexanone relative to the cyclohexane converted: 7.3%
(d) CS towards adipic acid relative to the cyclohexane converted: 58.9%
(e) CS towards adipic acid+cyclohexanone+cyclohexanol relative to the cyclohexane converted: 75.5%
(f) molar ratio of adipic acid/total of the diacids formed: 81.0%
(g) CS towards other compounds: 10.7%

Comparative Test 4

The procedure of Example 1 was repeated in the same apparatus and under the same operating conditions, but replacing the chromium acetate by the same molar amount of manganese acetate.

The following results were obtained:
(a) degree of conversion (DC) of the cyclohexane: 13.9%
(b) CS towards cyclohexanol relative to the cyclohexane converted: 17.1%
(c) CS towards cyclohexanone relative to the cyclohexane converted: 8.1%
(d) CS towards adipic acid relative to the cyclohexane converted: 54.2%
(e) CS towards adipic acid+cyclohexanone+cyclohexanol relative to the cyclohexane converted: 79.4%
(f) molar ratio of adipic acid/total of the diacids formed: 83.4%
(g) CS towards other compounds: 9.8%

Comparative Test 5

The following reactants:
(i) 47.4 g of acetic acid,
(ii) 0.25 g (2.54 mmol) of cyclohexanone,
(iii) 1.72 g (6.88 mmol of Co) of cobalt acetate tetrahydrate,
(iv) 0.194 g (1.11 mmol of Fe) of iron acetate,
were introduced into the apparatus described in Example 1. After closing the reactor, the mixture was stirred at 1,000 revolutions per minute, an air pressure (100 bar at 20° C.) was created and the reactor was heated. The temperature attained 105° C. in the bulk in 10 min and this temperature was maintained for an additional 50 min.

After cooling and depressurization, 10.1 g of cyclohexane were then added. After closing the reactor, a pressure of 100 bar of air was established and the reactor was heated to 105° C. with stirring at 1,000 revolutions/minute.

The mixture was permitted to react for 1 hour at 105° C. while maintaining the pressure constant using a reserve of pure oxygen.

After cooling and depressurizing the reactor, the reaction mixture comprised two liquid phases which were homogenized by adding acetic acid.

The homogeneous mixture thus obtained was assayed by gas chromatography.

The following results were obtained:
(a) degree of conversion (DC) of the cyclohexane: 40.9%
(b) CS towards cyclohexanol relative to the cyclohexane converted: 9.6%
(c) CS towards cyclohexanone relative to the cyclohexane converted: 0%
(d) CS towards adipic acid relative to the cyclohexane converted: 66.8%
(e) CS towards adipic acid+cyclohexanone+cyclohexanol relative to the cyclohexane converted: 76.4%
(f) molar ratio of adipic acid/total of the diacids formed: 81.1%
(g) CS towards other compounds: 8.2%

EXAMPLE 2

The procedure of Example 1 was repeated in the same apparatus, under the same temperature and pressure conditions and using the same reactants, but with a reaction time of 115 min.

The following results were obtained:
(a) degree of conversion (DC) of the cyclohexane: 15.0%
(b) CS towards cyclohexanol relative to the cyclohexane converted: 4.3%
(c) CS towards cyclohexanone relative to the cyclohexane converted: 0%
(d) CS towards adipic acid relative to the cyclohexane converted: 75.2%
(e) CS towards adipic acid+cyclohexanone+cyclohexanol relative to the cyclohexane converted: 79.5%
(f) molar ratio of adipic acid/total of the diacids formed: 83%
(g) CS towards other compounds: 5.0%

EXAMPLE 3

The procedure of Example 2 was repeated in the same apparatus, under the same operating conditions and using the same reactants, but adding 0.0049 g (0.01 mmol of Zr) of zirconium acetylacetonate and with a reaction time of 35 min.

The following results were obtained:
(a) degree of conversion (DC) of the cyclohexane: 14.1%
(b) CS towards cyclohexanol relative to the cyclohexane converted: 4.8%
(c) CS towards cyclohexanone relative to the cyclohexane converted: 10.0%
(d) CS towards adipic acid relative to the cyclohexane converted: 67.1%
(e) CS towards adipic acid+cyclohexanone+cyclohexanol relative to the cyclohexane converted: 81.9%

(f) molar ratio of adipic acid/total of the diacids formed: 84.5%

(g) CS towards other compounds: 5.8%

EXAMPLE 4

The procedure of Example 1 was repeated in the same apparatus and under the same operating conditions, but using 0.0672 g (0.29 mmol of Cr) of chromium acetate and with a reaction time of 115 min.

The following results were obtained:

(a) degree of conversion (DC) of the cyclohexane: 14.6%

(b) CS towards cyclohexanol relative to the cyclohexane converted: 4.5%

(c) CS towards cyclohexanone relative to the cyclohexane converted: 3.5%

(d) CS towards adipic acid relative to the cyclohexane converted: 72.9%

(e) CS towards adipic acid+cyclohexanone+cyclohexanol relative to the cyclohexane converted: 80.8%

(f) molar ratio of adipic acid/total of the diacids formed: 84.7%

(g) CS towards other compounds: 6.0%

EXAMPLE 5

The procedure of Example 1 was repeated in the same apparatus and under the same operating conditions, but using 0.0033 g (0.0145 mmol of Cr) of chromium acetate and with a reaction time of 60 min.

The following results were obtained:

(a) degree of conversion (DC) of the cyclohexane: 14.0%

(b) CS towards cyclohexanol relative to the cyclohexane converted: 7.6%

(c) CS towards cyclohexanone relative to the cyclohexane converted: 14.7%

(d) CS towards adipic acid relative to the cyclohexane converted: 59.4%

(e) CS towards adipic acid+cyclohexanone+cyclohexanol relative to the cyclohexane converted: 81.7%

(f) molar ratio of adipic acid/total of the diacids formed: 83.7%

(g) CS towards other compounds: 6.5%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a carboxylic acid, comprising oxidizing a cyclohexane with oxygen or an oxygen-containing gas, in liquid phase, in a solvent reaction medium which comprises a polar protic or aprotic solvent, and also in the presence of a catalytically effective amount of catalyst values dissolved in said solvent reaction medium, said catalyst values comprising at least one solvent-soluble cobalt compound and at least one solvent-soluble chromium compound.

2. The process as defined by claim 1, said at least one solvent-soluble cobalt compound comprising cobalt chloride, cobalt bromide, cobalt nitrate, a cobalt carboxylate, a cobalt chelate, or combination thereof.

3. The process as defined by claim 1, said at least one solvent-soluble chromium compound comprising chromium chloride, chromium bromide, chromium nitrate, a chromium carboxylate, a chromium chelate, or combination thereof.

4. The process as defined by claim 1, wherein the molar ratio between the chromium and the cobalt in said catalyst values ranges from 0.001 to 100.

5. The process as defined by claim 4, said molar ratio ranging from 0.01 to 10.

6. The process as defined by claim 1, said catalyst values further comprising at least one solvent-soluble zirconium and/or hafnium compound selected from among zirconium tetrachloride, zirconium bromide, zirconium nitrate, a zirconium carboxylate, a zirconium chelate, hafnium chloride, hafnium bromide, hafnium nitrate, a hafnium carboxylate, a hafnium chelate, or combination thereof.

7. The process as defined by claim 6, wherein the molar ratio between the zirconium and/or hafnium and the cobalt in said catalyst values ranges from greater than 0 to 10.

8. The process as defined by claim 7, said molar ratio ranging from 0.001 to 5.

9. The process as defined by claim 1, wherein the amount of catalyst values, expressed as a weight percentage of elemental cobalt and of elemental chromium relative to the total weight of the reaction mixture, ranges from 0.001% to 5%.

10. The process as defined by claim 9, said weight percentage ranging from 0.01% to 2.0%.

11. The process as defined by claim 1, said solvent reaction medium comprising an aliphatic carboxylic acid having from 2 to 9 carbon atoms, a perfluoroalkylcarboxylic acid, an alcohol, a halogenated hydrocarbon, a ketone, a lower alkyl ester of a carboxylic acid, tetramethylene sulfone (or sulfolane), acetonitrile, or combination thereof.

12. The process as defined by claim 11, said solvent reaction medium comprising acetic acid.

13. The process as defined by claim 1, said solvent comprising from 1% to 99% by weight of said solvent reaction medium.

14. The process as defined by claim 1, carried out at a temperature ranging from 50° C. to 200° C.

15. The process as defined by claim 14, carried out at a pressure ranging from 0.1 MPa (1 bar) to 20 MPa (200 bar).

16. The process as defined by claim 1, carried out in the presence of an oxidation reaction initiator.

17. The process as defined by claim 1, wherein the molar ratio of adipic acid to total of diacids formed is about 83% or higher.

18. A process for the preparation of a carboxylic acid, comprising oxidizing a cyclohexane, in the absence of an aldehyde, with oxygen or an oxygen-containing gas, in a liquid phase, in a solvent reaction medium which comprises a polar protic or aprotic solvent, and also in the presence of a catalytically effective amount of catalyst values dissolved in said solvent reaction medium, said catalyst values comprising at least one solvent-soluble cobalt compound and at least one solvent-soluble chromium compound.

* * * * *